United States Patent [19]
Yano et al.

[11] Patent Number: 5,668,370
[45] Date of Patent: Sep. 16, 1997

[54] AUTOMATIC IONIZATION MASS SPECTROMETER WITH A PLURALITY OF ATMOSPHERIC IONIZATION SOURCES

[75] Inventors: Masayoshi Yano; Tadao Mimura, both of Katsuta; Yoshiaki Kato, Mito, all of Japan

[73] Assignee: Hitachi, Ltd., Tokyo, Japan

[21] Appl. No.: 683,347

[22] Filed: Jul. 18, 1996

Related U.S. Application Data

[63] Continuation of Ser. No. 262,090, Jun. 20, 1994, abandoned.

[30] Foreign Application Priority Data

Jun. 30, 1993 [JP] Japan .................... 5-160517

[51] Int. Cl.⁶ .................... H01J 49/26
[52] U.S. Cl. .................... 250/288; 250/423 R; 250/285
[58] Field of Search .................... 250/288, 281, 250/282, 423 R, 285, 288 A

[56] References Cited

U.S. PATENT DOCUMENTS

| | | | |
|---|---|---|---|
| 3,723,730 | 3/1973 | Gordon et al. | 250/285 |
| 3,796,872 | 3/1974 | Merren | 250/285 |
| 4,960,991 | 10/1990 | Goodley et al. | 250/288 |
| 5,103,093 | 4/1992 | Sakairi et al. | 250/288 |
| 5,300,785 | 4/1994 | Aitken | 250/423 R |
| 5,315,118 | 5/1994 | Mous | 250/492.21 |

FOREIGN PATENT DOCUMENTS 56-21096  5/1981  Japan.

OTHER PUBLICATIONS

Hitachi Scientific Instrument News, '91, vol. 34, No. 1: *Hitachi Model M-1000 LC/MS Spectrometer*.

*Primary Examiner*—Kiet T. Nguyen
*Attorney, Agent, or Firm*—Kenyon & Kenyon

[57] ABSTRACT

An LC-MS is provided with a plurality of ion sources which can be quickly and selectively disposed at a fixed working position, and capable of analyzing a large variety of substances. An APCI unit (1) and an ESI unit (2) are fixedly mounted on a rotating table (11) or a sliding carriage (19). The rotating table (11) is held for rotation on a base (13) with a holding ring (12), and the sliding carriage (19) is held for linear sliding movement on a bearing (22) on a base (21) with a holding member (20) and is moved by a feed screw (23). Either the APCI unit (1) or the ESI unit (2) is selectively disposed at a fixed working position opposite to a first aperture (16), a second aperture (17) and a mass spectrometric unit (18) to ionize a substance for mass spectrometry. The plurality of ion sources can be set at the fixed working position by a simple setting operation, increases the variety of substances which can be analyzed, and enables the LC-MS to produce a plurality of mass spectra for a single substance to facilitate the analysis and the like of the molecular structure of the substance.

11 Claims, 5 Drawing Sheets

AUTOMATIC IONIZATION MASS SPECTROMETER WITH A PLURALITY OF ATMOSPHERIC IONIZATION SOURCES

This application is a continuation of application Ser. No. 08/262,090, filed Jun. 20, 1994, now abandoned.

FIELD OF THE INVENTION

The present invention relates to a mass spectrometer and, more particularly, to a mass spectrometer (hereinafter, abbreviated to "MS"), such as a liquid chromatographic mass spectrometer (hereinafter, abbreviated to "LC-MS"), for analyzing a variety of samples by using a plurality of ion sources, such as atmospheric chemical ionization ion sources (hereinafter, abbreviated to "APCI") and electrospray ionization ion sources (hereinafter, abbreviated to "ESI").

BACKGROUND OF THE INVENTION

There are several ionizing methods for the conventional LC-MS. Each ionizing method has its features and has difficulty in ionizing some substances.

A LC as a separating apparatus enables the measurement of a large variety of substances including low-polarizing substances and high-polarizing substances.

Various systems have been developed to deal with a variety of samples by a single ionizing method.

Those systems are described in Yoshiaki Karo et al., "Hitachi LC-MS analyzer M-1000", HITACHI SCIENTIFIC INSTRUMENT NEWS, Vol. 34, No. 1, (1991).

Each of those ionizing methods has certain features and is capable of ionizing only a specific group of samples and is incapable of ionizing all kinds of samples.

On the other hand, the LC-MS is desired to be able to analyze a variety of substances for LC.

Therefore, a MS provided with two ion sources has been proposed. A known art uses an API method and an ion source in combination to enhance ionizing efficiency.

This known art uses a main ion source of the API method and an auxiliary ion source of an electron impact type connected in series to the main ion source and ionizes neutral molecules which could not be ionized by the API by electron impact to increase the quantity of ions so that the sensitivity of mass spectrometer is substantially enhanced. Techniques relating to this known art is disclosed in Japanese Patent No. 1078632.

A LC-MS provided with an atmospheric ionization ion source and a chemical ionization ion source which are used selectively to analyze a variety of substances has been proposed. Techniques relating to this LC-MS are disclosed in Japanese Patent Laid-open (Kokai) No. 4-109160.

Although the aforesaid known MS is provided with two ion sources, there are restrictions on the operating condition of the sample supply system, and only a limited number of combinations of two ion sources are possible. Therefore, the MS is able to analyze limited substances and is unable to utilize the advantageous capability of separating a variety of substances of a LC, even if the MS is connected directly to the LC.

No attempt was made to use the MS in combination with an ESI method that exhibits an excellent function in ionizing ionic, high-polarizing compounds and hence the MS is incapable of analyzing polymeric compounds.

The present invention has been made to solve those problems in the related art and it is therefore an object of the present invention to provide an atmospheric ionization MS provided with a plurality of ion sources to be selectively used, connected directly to a LC capable of analyzing a variety of substances to utilize the advantages of the LC, and capable of measuring a variety of objects.

SUMMARY OF THE INVENTION

With the foregoing object in view, the present invention provides an atmospheric ionization mass spectrometer to atomize and ionize substances separated by the liquid chromatographic apparatus for mass spectroscopy, comprising a plurality of atmospheric ionization ion sources for atomizing and ionizing the substances separated by the liquid chromatographic apparatus, and a selector switch for selecting a desired one of the plurality of atmospheric ionizing ion sources.

Each of the atmospheric ionization ion sources is either a combination of an atmospheric chemical ionization ion source and an electrospraying ionization ion source, or a combination of an atmospheric chemical ionization ion source and another type of atmospheric ionization ion source.

The selecting means for selecting a desired one of the plurality of ion sources selects one of the ion sources and may dispose the selected ion source at a fixed working position by a mechanical means.

The selecting means for selecting a desired one of the plurality of ion sources selects one of the ion sources and may dispose the selected ion source at the fixed working position by an electrical means.

The selecting means for selecting a desired one of the plurality of ion sources selects one of the ion sources and may dispose the selected ion source at the fixed working position by an electrical means, and adjusts the position of the ion source for fine positional adjustment by a mechanical means.

The mechanical means for disposing the selected ion source at the fixed working position may turn the ion sources along a fixed path.

The mechanical means for disposing the selected ion source at the fixed working position may reciprocate the ion sources along a fixed path.

The foregoing technical means function as follows.

The atmospheric ionization mass spectrometer is provided with, for example, an atmospheric chemical ionization ion source suitable for ionizing low-polarizing and medium-polarizing substances and an electrospray ionization ion source suitable for ionizing high-polarizing substances, each ion source is operated to inject a plurality of kinds of ions into the mass spectrometric unit, and the mass spectrometric unit analyzes the ions to enable the liquid chromatographic mass spectrometer to deal with an increased kinds of substances.

DETAILED DESCRIPTION

Preferred embodiments of the present invention will be described hereinafter with reference to FIGS. 1 to 8.

[First Embodiment]

Figure 1:
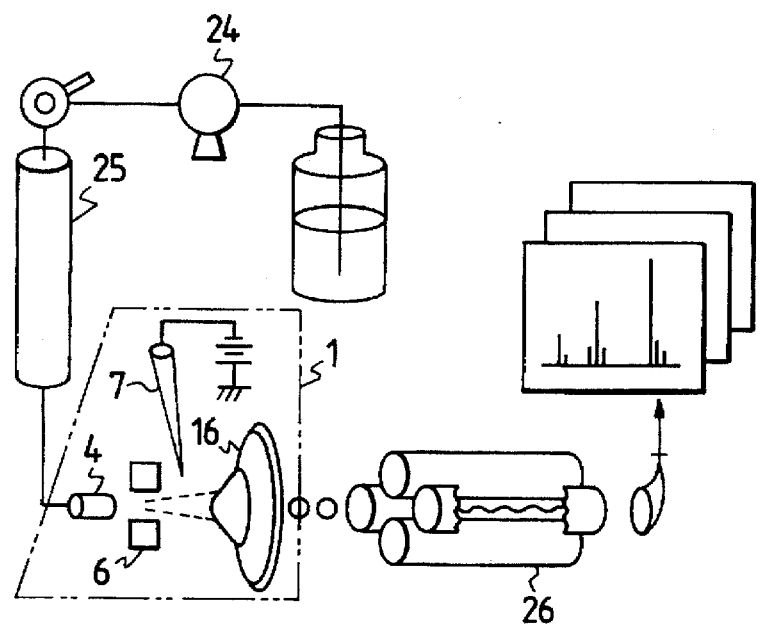
FIG. 1 is a diagrammatic view of a LC-MS incorporating an APCI.
Figure 2:
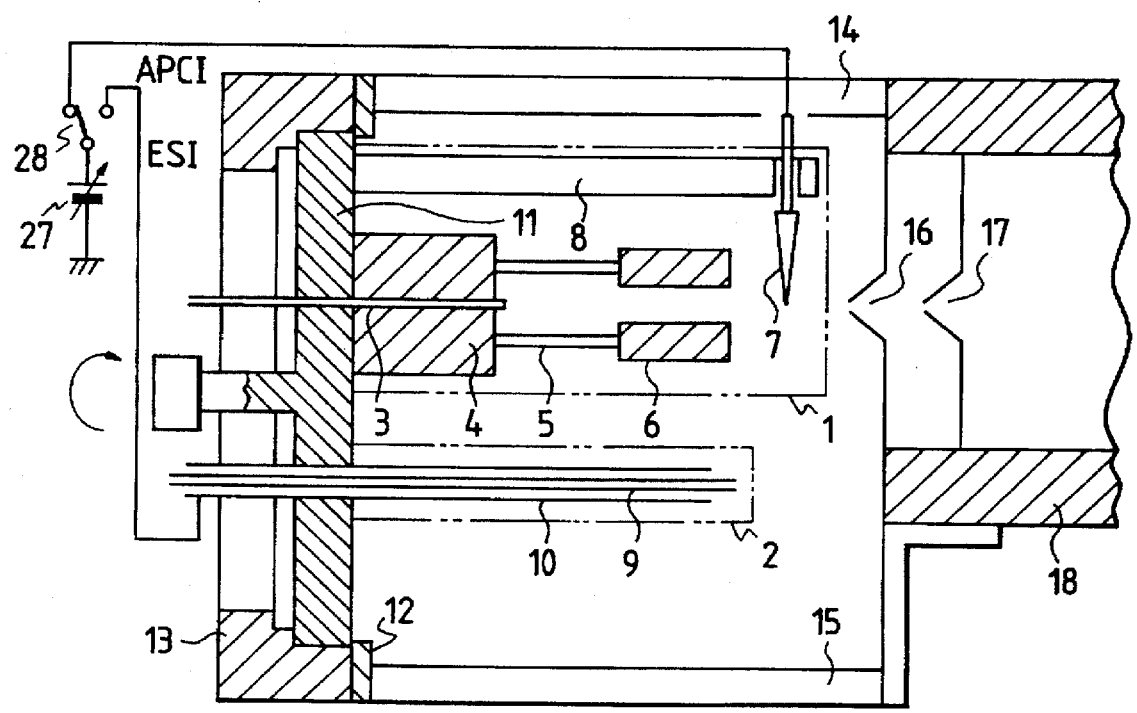
FIG. 2 is a longitudinal sectional view of ion sources included in an atmospheric ionization mass spectrometer.

Referring to FIGS. 1 and 2, there are shown an APCI unit 1, an ESI unit 2, a discharge pipe 3, an atomizer 4, a support bar 5, a solvent removing chamber 6, a needle electrode 7, a support bar 8, a discharge pipe 9, a gas supply pipe 10, a rotating table 11, a holding ring 12, a base 13, support bars 14 and 15, a first aperture 16, a second aperture 17, a mass spectrometric unit 18, a sliding carriage 19, a holding member 20, a base 21, a bearing 22, a feed screw 23, a LC pump 24, a LC column 25, a mass spectrometer 26, a power source 27, and a selector switch 28.

The LC-MS incorporating the APCI unit will be described briefly with reference to FIG. 1.

Referring to FIG. 1, the LC pump 24 feeds a sample solution into the LC column 25, and the LC column 25 separates the sample solution and the separated sample solutions is fed into the APCI unit 1.

The sample solution fed into the APCI unit 1 is atomized by the atomizer 4, and molecules of the solvent are removed in the solvent removing chamber 6.

The atomized sample not containing any solvent is subjected to corona discharge produced by applying a voltage of about 3 kV across the needle electrode 7 and the first aperture 16 to ionize the molecules of the solvent. The molecules of the sample are ionized by the ion-molecule reaction between the ions of the solvent and the molecules of the sample, and the ions of the sample are subjected to mass spectrometry on the mass spectrometer 26.

The atmospheric ionization mass spectrometer in the first embodiment according to the present invention will be described hereinafter.

A constitution formed by directly connecting a MS and a LC, and the operation of the same are the same as those described with reference to FIG. 1, and hence the description thereof will be omitted to avoid duplication.

The ion source of the atmospheric ionization mass spectrometer will be described hereinafter.

As shown in FIG. 2, the APCI unit 1 and the ESI unit 2 are fixedly mounted on the rotating table 11.

The APCI unit 1 comprises the discharge pipe 3 through which the sample solution is discharged from the LC, not shown, the atomizer 4 for atomizing the sample solution, the solvent removing chamber 6 for removing molecules of the solvent from the sample solution, supported on the support bars 5, the needle electrode 7 for producing corona discharge, supported on the support bar 8, and the power source 27 for applying a voltage to the needle electrode 7.

The ESI unit 2 comprises the discharge pipe 9 for discharging the sample solution from the LC, not shown, and the gas supply pipe 10 through which the discharge pipe 9 is extended. The gas supply pipe 10 extends through the rotating table 11, and a voltage is applied to the gas supply pipe 10 by the power source 27.

The selector switch 28 changes the connection of the power source 27 to apply the voltage to either the APCI unit 1 or the ESI unit 2. The supply voltage of the power source 27 is variable.

The rotating table 11 is supported for rotation by the support bars 14 and 15 and held on the base 13 by the holding ring 12.

The rotating table 11 is turned to dispose either the solvent removing chamber 6 of the APCI unit 1 or the discharge pipe 9 of the ESI unit 2 opposite to the first aperture 16 and the second aperture 17 so that streams of ions flow toward the first aperture 16 and the second aperture 17, through which communication to the mass spectrometric unit 18 is established.

Thus, ions produced by the APCI unit 1 and the ESI unit 2 flow through the first aperture 16 and the second aperture 17 into the mass spectrometric unit 18.

In FIGS. 1 and 2, the APCI unit 1 is disposed opposite to the first aperture 16, the second aperture 17 and the mass spectrometric unit 18 to analyze the sample supplied by the APCI unit 1.

When the rotating table 11 is turned to dispose the ESI unit 2 opposite to the first aperture 16, the second aperture 17 and the mass spectrometric unit 18, and the selector switch 28 disconnects the APCI unit 1 from the power source 27 and connects the ESI unit 2 to the power source 27 to apply a voltage across the needle electrode 7 and the gas supply pipe 10, the sample ionized by the ESI unit 2 is subjected to analysis.

Thus the switching between the APCI unit 1 and the ESI unit 2 is made possible and samples ionized by each ionization method are analyzed.

For switching ion source, the measurement condition (drift voltage and temperature in the ionization chamber) of ion sources may be set previously or may be set for individual measurements.

Generally, the ionization by the APCI is suitable to analyze low polarizing substances like amino acids. On the other hand, the ionization by the ESI is suitable to analyze high molecular compounds like proteins. As these examples, a specific ionization method corresponds to a specific sample to be measured, and it is desirable to select an ionization method depending on the sample to be measured.

In this system, at first, a sample is mass-analyzed using the ionization by the APCI and then analyzed using the ionization by the ESI. Based on the result of mass spectrometry, it is identified whether either the analysis by the APCI or by the ESI alone satisfies the purpose or both analyses by the APCI and by the ESI are necessary for the purpose. According to the identification, the system will select the suitable ion source for mass spectrometry from the next analysis.

Figure 3A:
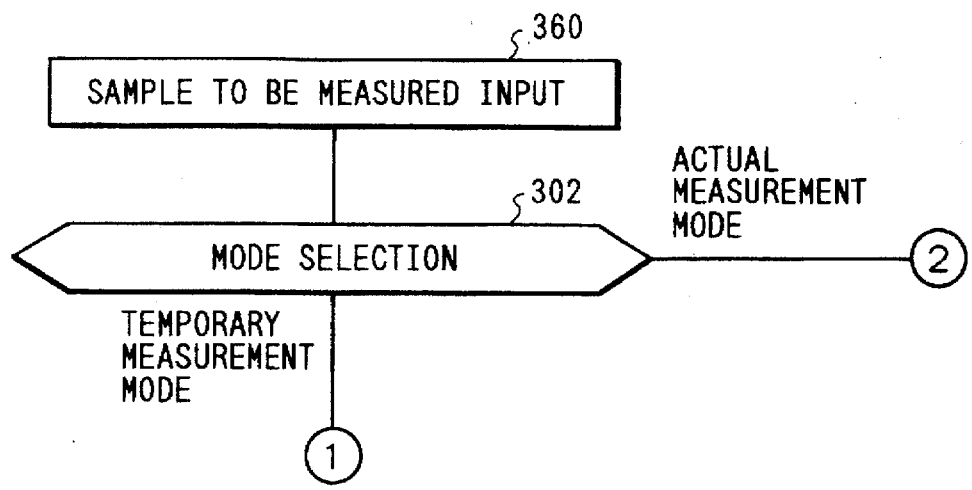
FIGS. 3(a) to 3(c) are flowcharts showing the analytical operation.

At the step 300 in FIG. 3(a), an operator inputs the kind of the sample to be subjected to the measurement. The kind of the sample to be measured is stored. At the step 302, the operator selects the mode, that is, selects either a temporary measurement mode or an actual measurement mode. The temporary mode is a mode for identifying whether either the APCI or the ESI alone is suitable or both the APCI and ESI are necessary with respect to the sample.

Figure 3B:
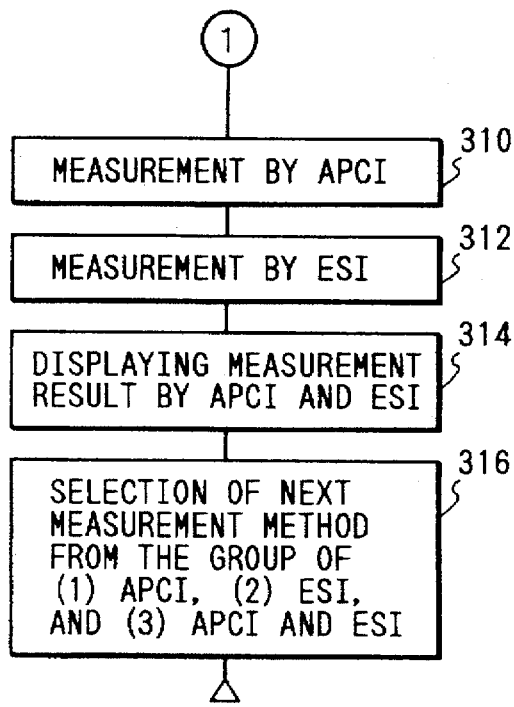

When the temporary mode is selected at the step 302, the analysis continues to the flowchart of FIG. 3(b), and at the step 310 the rotating table 11 (FIG. 1) is rotated to ionize the sample in the APCI unit 1. The actual mass spectrometry is carried out and the analytical result is stored.

Then at the step 314 the rotating table 11 (FIG. 1) is rotated to ionize the sample in the ESI unit 2. Also the actual mass spectrometry is carried out and the analytical result is stored.

Figure 4A:
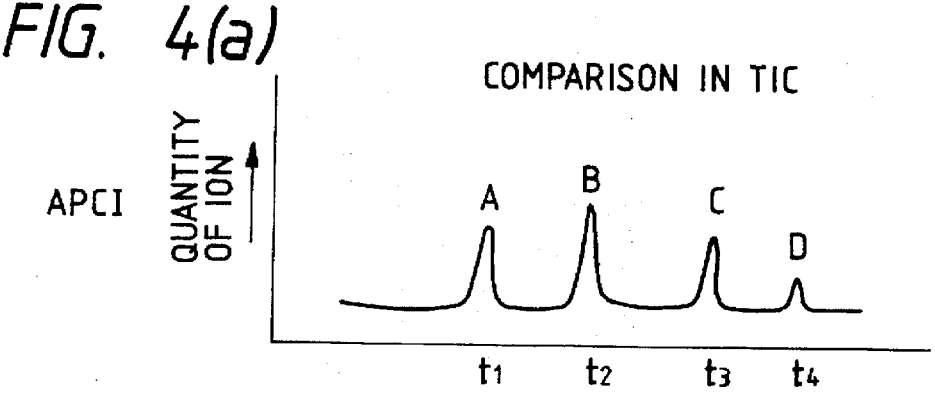
FIGS. 4(a) and 4(b) are charts showing TIC of the APCI and the ESI respectively.
Figure 4B:
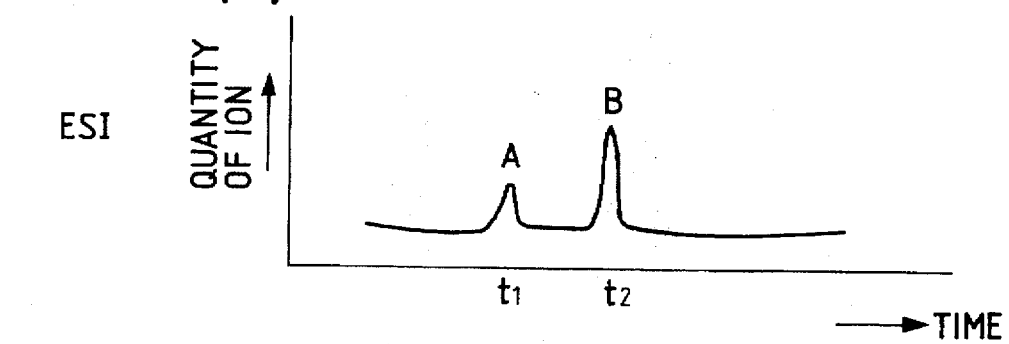
Figure 5A:
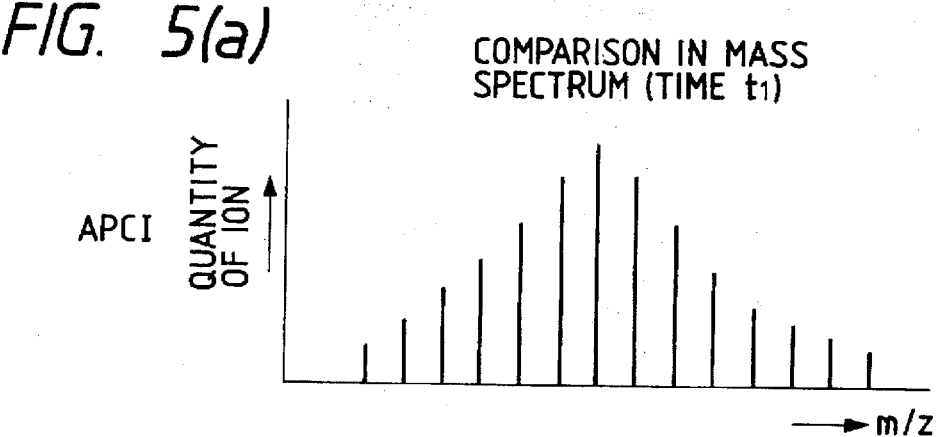
FIGS. 5(a) and 5(b) are charts showing spectrum of the APCI and the ESI respectively.
Figure 5B:
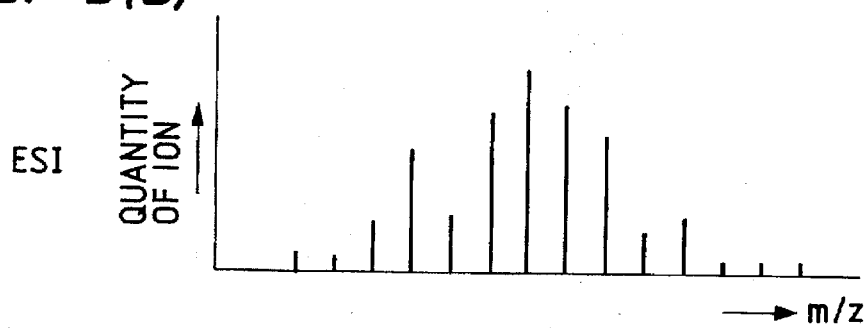

At the step 314, the analytical result by the APCI and the analytical result by the ESI are displayed on the screen of the display. That is, at first TIC (Total Ion Current: total signal value within a specified period of time (quantity of ion)) by the APCI and the ESI is displayed as shown in FIG. 4, where it is preferable to use different colors for the APCI and the ESI for easy recognition. In the example of FIG. 4, at the time $t_1$ the quantity of ion detected by the APCI is considerably greater than that detected by the ESI. At the time $t_2$ the comparison indicates that the both exhibit similar results. At the later time $t_3$ and $t_4$, only APCI detects ions. In mass spectra shown in FIG. 5 the quantity of ion detected by the APCI is greater than that detected by the ESI over the entire range of m/Z. This means that sufficient information is obtained by the APCI but not by the ESI.

Figure 6:
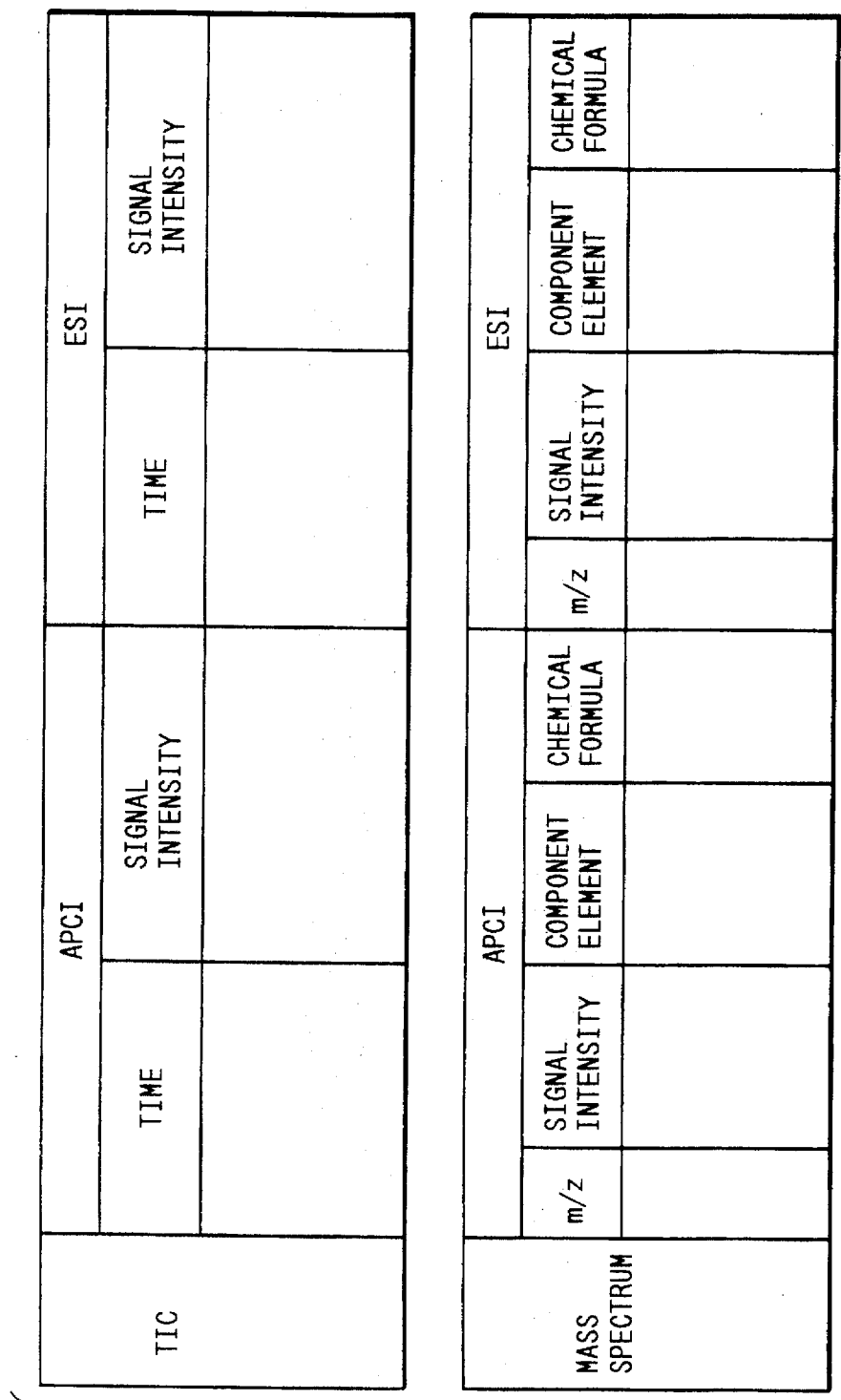
FIG. 6 is a table showing analytical results.

As shown in FIG. 6, on the screen of the display signal intensity (quantity of ion) at the individual time, signal intensity (quantity of ion) at the individual m/Z, component elements, and chemical formulae for the APCI and the ESI respectively are shown in the form of numerals.

At the step 316, based on this information the operator selects an ionization method suitable for samples, that is, selects either the APCI or the ESI alone or both the APCI and ESI, and this information is stored. From this analytical result, ionization conditions such as drift voltage and ionization chamber temperature, corresponding to the sample, may be set. In the above example, the APCI is more preferable than the ESI, but in some cases the ESI may be more preferable than the APCI. In some cases it may be necessary to employ mass analyses by both the APCI and the ESI. For example in FIG. 4, if A at the time $t_1$ and C at the time $t_3$ are detected without detection of B and D for the APCI, and B at the time $t_2$ and D at the time $t_4$ are detected without detection of A and C for the ESI, in this case both the APCI and ESI are necessary. Measurements are carried out by both the APCI and ESI, the mass spectra are combined, and the analytical result based on both measurements is important.

The operator selects a method from either the APCI or the ESI or both the APCI and ESI, but for more convenience the selection may be made automatically by previously storing a program for selection.

Figure 3C:
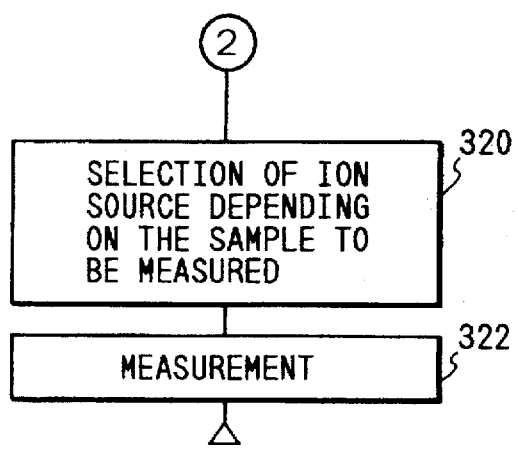

At the step 302 in FIG. 3(a), the actual measurement mode being selected, an ion source is selected depending on the sample to be measured at the step 320 in FIG. 3(c) based on the selection (stored) at the step 316. Where, if the sample is analyzed without passing through the temporary measurement mode, based on the relation shown in FIG. 7, either the APCI or the ESI is selected automatically. Otherwise, the operator may select. At the step 322, the mass analysis is carried out, for example, both analyses by the APCI and by the ESI are carried out, both results are combined, and an analytical result based on both results is displayed on the screen.

Figure 7:
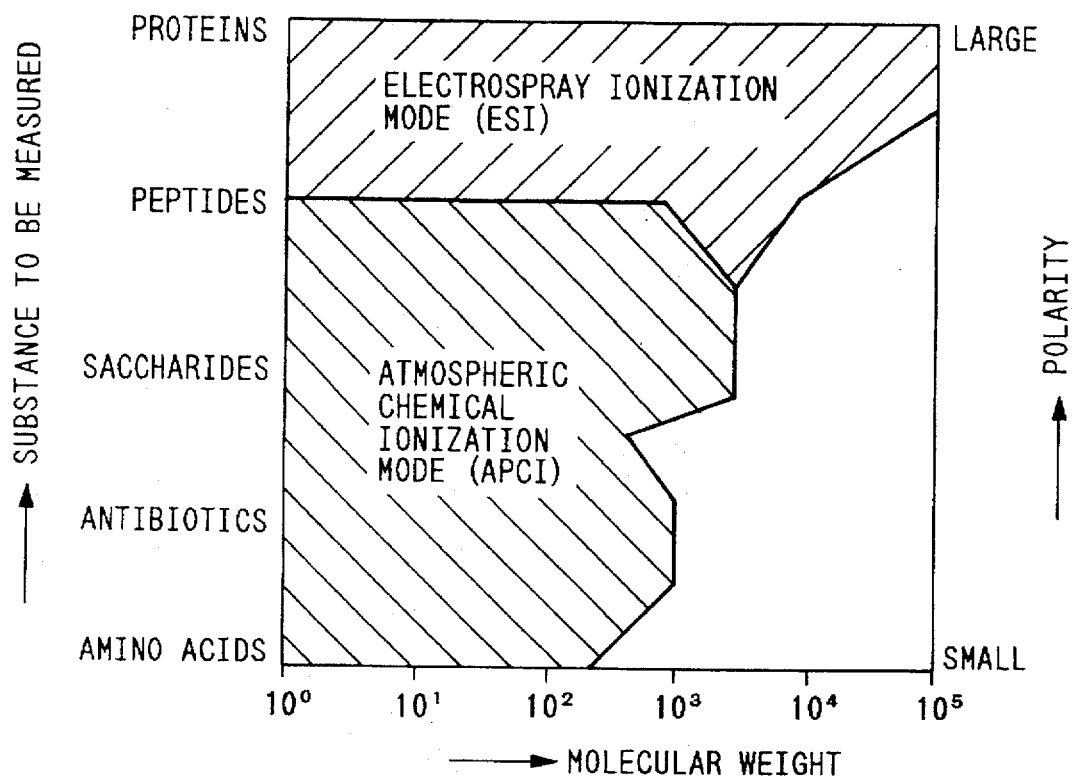
FIG. 7 is a graph showing the ion source selection corresponding to substances to be analyzed.

FIG. 7 is a graph showing substances which can be ionized by the APCI and the ESI employed in the foregoing embodiments, in which the names of substances are indicated on the vertical axis, the molecular weight is measured on the horizontal axis, and the APCI and the ESI can be used for ionizing the substances in the shaded areas.

The APCI is suitable for ionizing amino acids, antibiotics, saccharides and such having a molecular weight in the range of 1000 to 2000 dalton, and the ESI is suitable for ionizing peptides, proteins and such having a molecular weight on the order of 100,000 dalton or above. In the embodiments of the present invention, the APCI and the ESI can be selectively used by a simple setting operation.

Most of those substances are analyzed by the LC, and the advantages of the use of the MS in the LC-MS is beyond expectation.

[Second Embodiment]

An ion source employed in an atmospheric ionization mass spectrometer in a second embodiment according to the present invention will be described hereinafter.

Figure 8:
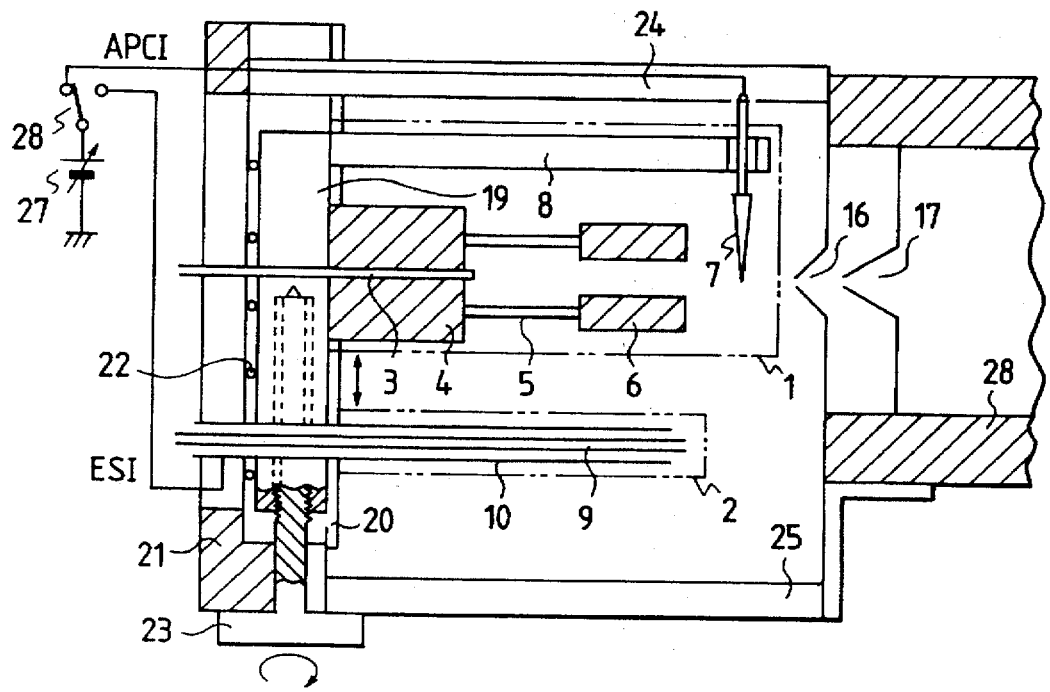
FIG. 8 is a longitudinal sectional view showing an ion source of LC/MS in the second embodiment.

In FIG. 8, parts like or corresponding to those shown in FIG. 1 are denoted by the same reference characters, and the description thereof will be omitted. In FIG. 8, there are shown new components including a sliding carriage 19, a holding member 20, a base 21, a bearing 22, a feed screw 23 and support bars 24 and 25.

An APCI unit 1 and an ESI unit 2, which are the same as those employed in the first embodiment, are fixedly mounted on the sliding carriage 19.

The sliding carriage 19 is held for reciprocation with the holding member 20 serving also as a guide on the bearing 22 on the base 21 supported on the support bars 24 and 25.

A knob attached to the feed screw 23 is turned to advance and retract the sliding carriage 19. In FIG. 8, the APCI unit 1 is positioned for operation opposite to the first aperture 16, the second aperture 17 and the mass spectrometric unit 18.

When the sliding carriage 19 disposes the ESI unit 2 at the fixed working position opposite to the first aperture 16, the second aperture 17 and the mass spectrometric unit 18, the selector switch 28 disconnects the power source 27 from the APCI unit 1 and connects the same to the ESI unit 2 to enable the analysis of the sample.

Although the foregoing embodiments are provided with the mechanical means for disposing one of the plurality of ion sources at the fixed working position, an electrical means may be used instead of the mechanical means. For example, each of the ion sources is disposed at the fixed working position electrically.

A mechanical means and an electrical means may be used in combination instead of the mechanical means or the electrical means. For example, each of the ion sources may be selectively disposed at the fixed working position by an electrical means, and the position of the ion source may be adjusted for fine adjustment by a mechanical means.

The foregoing embodiments have the following concrete effects.

(1) One of the plurality of ion sources, such as the APCI and the ESI, can be easily, quickly and selectively disposed at the fixed working position by a simple operation without requiring any replacing operation. While the conventional atmospheric ionization mass spectrometer requires sixty minutes for an operation to replace one ion source with another, the atmospheric ionization mass spectrometer embodying requires about three minutes for the same operation.

(2) The utilization of the advantages of the plurality of ion sources, such as the APCI and the ESI, increases the kinds of substances which can be analyzed by the atmospheric ionization mass spectrometer.

(3) The plurality of ionizing systems, such as the APCI and the ESI, can be used for ionizing a sample substance and hence different mass spectra can be obtained for the sample substance, which increases the amount of information to facilitate the analysis of the molecular structure of the sample substance.

As is apparent from the foregoing description, the atmospheric ionization mass spectrometer in accordance with the present invention is provided with a plurality of ion sources which can be quickly and selectively disposed at the fixed working position. The use of the plurality of ion sources expands the range of application of the atmospheric ionization mass spectrometer, and the advantages of the atmospheric ionization mass spectrometer is utilized effectively when the atmospheric ionization mass spectrometer is used in combination with a LC.

What is claimed is:

1. An atmospheric ionization mass spectrometer apparatus comprising:

a mass spectrometer having a mass spectrometric portion with an opening;

a liquid chromatographic apparatus separating substances for mass spectroscopy by said mass spectrometer;

first and second atmospheric ionization ion sources atomizing and ionizing the substances separated by the liquid chromatographic apparatus, wherein said first source is a different type of source than said second source; and a selector switch selectively disposing one of said first source and said second source at a time at a fixed working position opposite said opening to said mass spectrometric portion.

2. The atmospheric ionization mass spectrometer apparatus according to claim 1, wherein said first and second atmospheric ionization ion sources include an atmospheric chemical ionization ion source and an electrospraying ionization ion source.

3. The atmospheric ionization mass spectrometer apparatus according to claim 1, wherein said selector switch selects one of the ion sources and disposes the selected ion source at said fixed working position by a mechanical means.

4. The atmospheric ionization mass spectrometer apparatus according to claim 3, wherein the mechanical means for disposing the selected ion source at the fixed working position turns the ion sources along a fixed path.

5. The atmospheric ionization mass spectrometer apparatus according to claim 3, wherein the mechanical means for disposing the selected ion source at the fixed working position moves the ion sources linearly along a fixed path.

6. The atmospheric ionization mass spectrometer apparatus according to claim 1, wherein said selector switch selects one of the ion sources and disposes the selected ion source at the fixed working position by an electrical means.

7. The atmospheric ionization mass spectrometer apparatus according to claim 1, wherein said selector switch selects one of the ion sources and disposes the selected ion source at the fixed working position by an electrical means, and adjusts the position of the ion source for the positional adjustment by a mechanical means.

8. The atmospheric ionization mass spectrometer apparatus according to claim 1, wherein the ion source is selected based on the respective ionization type.

9. The atmospheric ionization mass spectrometer apparatus according to claim 1, wherein the ion source is selected depending on the substances.

10. A mass spectrometer, comprising:

first and second atmospheric ionization ion sources, wherein said first source is a different type of source than said second source;

a selector switch selecting one of said first source and said second source; and a mass analyzer mass-analyzing ionized substances from said one of said first and second sources at a time selected by said selector switch and disposed opposite from an entrance to a mass spectrometric portion.

11. The mass spectrometer according to claim 10, wherein said mass spectrometer ionizes the substances by said first and second sources.

* * * * *

UNITED STATES PATENT AND TRADEMARK OFFICE
CERTIFICATE OF CORRECTION

PATENT NO. : 5,668,370
DATED : Sept. 16, 1997
INVENTOR(S) : Masanori OGINO

It is certified that error appears in the above-identified patent and that said Letters Patent is hereby corrected as shown below:

| Column | Line | |
|--------|------|---|
| 1 | 29 | Change "Karo" to --Kato--. |
| 3 | 3 | After "analyzed." delete "and". |

Signed and Sealed this

Seventeenth Day of February, 1998

Attest:

BRUCE LEHMAN

Attesting Officer    Commissioner of Patents and Trademarks